United States Patent
Hood

[19]

[11] Patent Number: 5,919,356
[45] Date of Patent: Jul. 6, 1999

[54] FLUID SAMPLING DEVICE

[75] Inventor: Robert Gordon Hood, Lochwinnoch, United Kingdom

[73] Assignee: FSM Technologies Ltd., Clydebank, United Kingdom

[21] Appl. No.: 08/860,079

[22] PCT Filed: Dec. 22, 1995

[86] PCT No.: PCT/GB95/03031

§ 371 Date: Jun. 24, 1997

§ 102(e) Date: Jun. 24, 1997

[87] PCT Pub. No.: WO96/20402

PCT Pub. Date: Jul. 4, 1996

[30] Foreign Application Priority Data

Dec. 24, 1994 [GB] United Kingdom .................... 9426251

[51] Int. Cl.⁶ .......................... B01D 17/12; B01D 63/04; G01N 21/15; G01N 1/10
[52] U.S. Cl. ...................... 210/85; 73/863.23; 210/136; 210/500.23; 422/58; 422/100; 422/101; 604/403
[58] Field of Search ................ 210/85, 94, 136, 210/321.6, 500.23, 416.1, 321.79, 321.8, 321.83, 321.88, 321.89; 422/101, 58, 59, 100, 103; 436/177, 178; 73/863, 23; 604/403, 404, 406

[56] References Cited

U.S. PATENT DOCUMENTS

| | | | |
|---|---|---|---|
| 3,539,300 | 11/1970 | Stone | 422/101 |
| 3,586,064 | 6/1971 | Brown et al. | 422/101 |
| 3,607,093 | 9/1971 | Stone | 422/101 |
| 3,682,596 | 8/1972 | Stone | 422/101 |
| 3,785,772 | 1/1974 | Coggeshall | 422/101 |
| 3,848,580 | 11/1974 | Hyden et al. | |
| 3,954,614 | 5/1976 | Wright | 210/136 |
| 4,978,504 | 12/1990 | Nason | 422/101 |
| 5,474,902 | 12/1995 | Uylen et al. | 422/101 |

FOREIGN PATENT DOCUMENTS

| | | |
|---|---|---|
| 0 315 252 | 5/1989 | European Pat. Off. . |
| 0 549 341 A1 | 6/1993 | European Pat. Off. . |
| 0 550 950 A2 | 7/1993 | European Pat. Off. . |
| 41 32 480 A1 | 4/1993 | United Kingdom . |
| WO 91/08782 | 6/1991 | WIPO . |

Primary Examiner—Joseph W. Drodge
Attorney, Agent, or Firm—Ratner & Prestia

[57] ABSTRACT

A portable device for sampling fluid. The device has a puncture device attached to a housing which has an interior and exterior wall. The housing is in fluid communication with the syringe and contains a filtration device comprised of at least one U-shaped hollow fiber membrane. The device also includes a collection chamber. Also in the device is a sensing device including a further hollow fiber membrane the first and second ends each connected to a first and second plug. Each of the plugs contacts the interior wall of the housing. The further hollow fiber membrane contains a sensing agent. The device is arranged so that a sample is collected through the puncture device and is passed through the filtration device where is it passed through the one or more U-shaped hollow fiber membrane to the collection chamber. From the collection chamber it is passed through the hollow fiber membrane which contains the sensing agent device before being passed to a syringe.

3 Claims, 3 Drawing Sheets

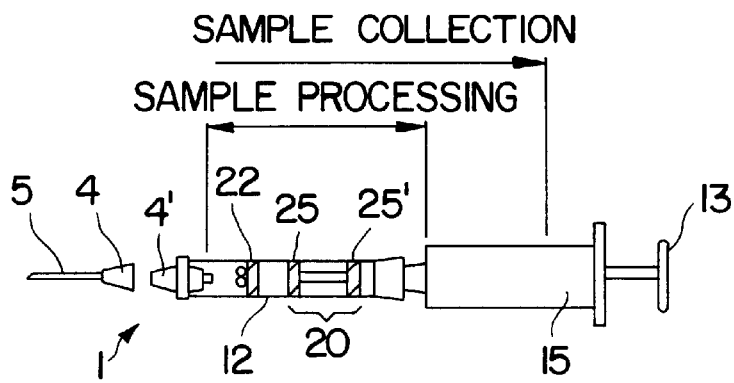
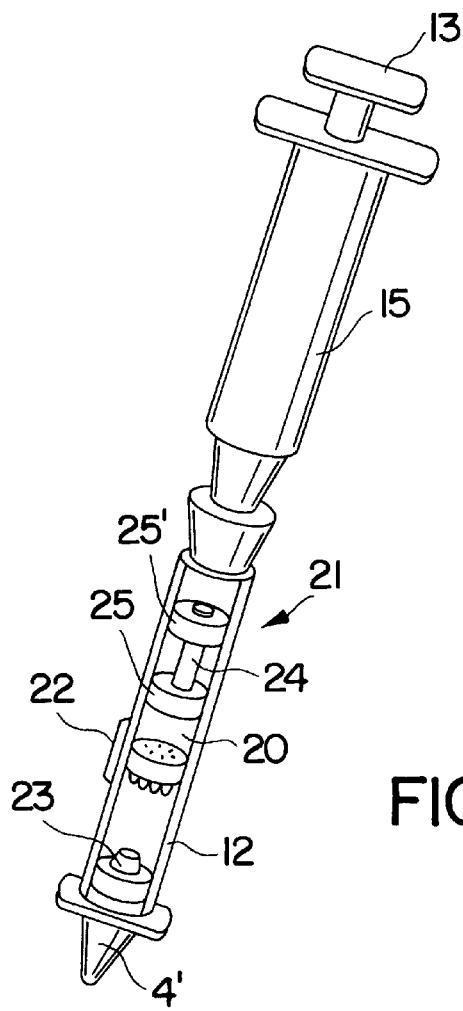
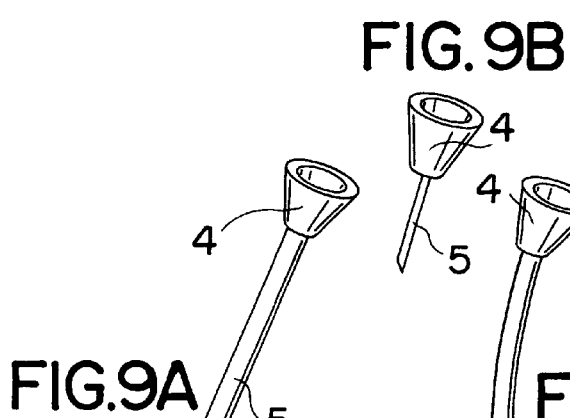
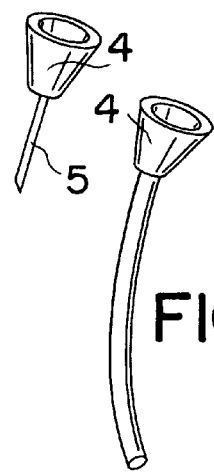
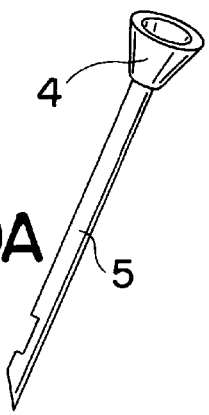

FLUID SAMPLING DEVICE

This invention relates to a device for sampling fluids, and in particular concerns a device which can obtain a sample of a fluid (such as blood), filter the sample, and perform an assay on the filtrate to detect the presence of a particular component therein, such as a pathogen.

Conventional blood-sampling devices are not known to comprise filter means for separating the blood components before testing. Thus, to be tested for the presence of viral proteins, the blood must first be extracted from the patient, separated into serum and cells, for example by centrifugation, and the serum assayed in a separate vessel. This can be time consuming and can therefore add to the costs involved in a diagnostic testing procedure.

In addition, current blood sampling devices generally comprise puncturing means which pierce the skin of a patient and extract a relatively high volume of blood from the patient, for example a needle and syringe arrangement whereby the needle pierces the skin and enters a blood vessel and blood is extracted from the paitent into the syringe body. This can be traumatic for the patient and an unnecessarily high volume of blood can be taken, most of which is not required for sampling.

The present invention provides a device for sampling a fluid, the device having filtration means for separating components of the fluid, a conduit directing flow of the fluid to be sampled from a source through the device, and sensing means which can detect the presence of a component in the fluid.

The relatively small size of the device ensures it's portability and the device will normally be shaped and dimensioned so to be convenient to hand-hold. The device will normally be a single-use disposable item.

In certain embodiments the device has puncture means such as a hypodermic needle to pierce the skin of a patient and allow the sampling of blood, synovial fluid or other body fluids therefrom. Biopsy needles or small bore needles may be used as a puncture means in the device. Fluid may also be extracted directly from tissue by exerting pressure on the tissue; this extraction may occur in situ or using a sample excised from the patient's body.

Alternatively, the fluid may be sampled non-invasively and thus a puncture means may be unnecessary. For example the fluid may be tears, urine or saliva, all of which can be sampled non-invasively. Thus the device may have a nozzle or other means to enable access into areas of restricted access.

Where present, the puncture means is desirably hollow and may be linked to the conduit.

The conduit can simply comprise the filtration means in the form of a hollow membrane fibre through which the body fluid can flow, or a bundle of such fibres. The device may also have a chamber for collecting the filtrate. The chamber may also contain the sensing means.

The fluid may comprise a liquid or a gas. In one embodiment the fluid may be a physiological sample such as blood, synovial fluid, tissue fluid, urine, tears, saliva etc. The fluid may also consist of a tissue sample, dissolved or suspended in a liquid medium.

However, the device may also be applied in non-medical or non-veterinary applications. For example the device may be used to sample fluids such as river wayter, sewage, industrial fluids or effluent, foodstuffs (for example milk, cheese, yogurt, beer, meat or fish).

Filtration of the sample preferably access through cross-flow filtration.

The filtration means may be woven or non-woven and can optionally comprise a membrane filter having pore sizes selected to separate, for example, blood cells from other blood components. The filtration means can be selected to filter out a particular molecule size range so that only a particular size range of molecule is present in the filtrate.

In one embodiment of the invention, the filtration means comprises a membrane filter in the form of a hollow membrane fibre or a bundle of such fibres through which the body fluid flows, so that filtration of the fluid occurs by cross-filtration, i.e., by flow of fluid along the surface of the filtration means, rather than perpendicularly towards the filtration means. The filtration means can also comprise a sheet of membrane filter which extends either transversely across or longitudinally along the lumen of the conduit or chamber, and preferably separates the needle from the sensing means.

The filtration means for use in the apparatus of the invention way be of any convenient shape and mention may be made of hollow membrane fibres and flat sheet membranes. Hollow membrane fibres or bundles of such fibres may be preferred in certain situations since this form permits a relatively large surface area through which filtration may occur. For other applications, however, flat membrane sheets (or layers of such sheets) may be preferable.

The filtration means may be made of any convenient material and the present invention is not limited with regard to the filtration means to be used. Generally the filtration means will be selected for the pore size of the filter. Ceramic filters, for example, may filter particles of diameter $5.0\ \mu m$ to $0.1\ \mu m$ and hollow fibre membranes may filter molecules of 1 mDa to 5 kDa. Suitable membranes are available commercially and may be made of polysulphone, cellulose, cellulose diacetate, polypropylene and/or ceramics materials.

In one embodiment the filtration means is in the form of a membrane embedded in a holding means located within the device. For example, hollow fibre membranes, bent into a "U" shape, may be embedded in a holder, for example a plug formed from cured adhesive.

The plug forms a close fit with the internal walls of a conduit within the filtration device. Reference may be made to the co-pending PCT Patent Application in the name of FSM Technologies Ltd filed Dec. 5, 1995, claiming priority from GB9424703.8, (incorporated herein by reference) as describing suitable membrane filtration means.

This embodiment allows the use of a membrane having a greater filtration surface area than the cross-sectional filtration area of the conduit. Generally the membrane in the filtration means is essentially three-dimensional. The membrane may have any convenient shape or configuration.

The term "cross-sectional filtration area" refers to the area of a cross-section of the conduit over which filtration occurs. Normally this would be the area of the lumen of the conduit. It may be possible to locate the filtration means part way along the length of the lumen. If the walls of the conduit are sloping (and therefore the cross-sectional area of the conduit varies) the "cross-sectional filtration area" is the cross-sectional area of the conduit at the point where the filtration means is located.

It is important that part of the membrane of the filtration means communicates with the exterior sides of the holder so that the sample entering the device (optionally under pressure) can be separated, the filtrate optionally being collected in a collection chamber.

In more detail the filtration means of the present invention may be formed from hollow fibre membranes which are wound round to form a spiral which is held in a holder. The spiral may be either two dimensional, that is forms a flat coil, or may be three-dimensional in which case the spiral is wound upwardly into a apex.

Alternatively the filter may be formed from "U"-shaped hoops of hollow membrane fibres. Preferably several hoops, for example over 10 hoops, especially 20 to 50 hoops, are present in each filtration means. The ends of each hoop pass through and are held by the holder.

The filter may be formed into hoops as described above, but the upper portion of the hoops are bent into an acute angle, thus forming an inverted "V" shape. The angle may conveniently be introduced into the membrane by spot application of heat which welds the sides of the membrane together at the point where heat is applied, thus forming a hinge.

In another embodiment, hollow fibre membranes each having a "blind" or closed end may be used. In one arrangement the blind ends ends be exposed to the sample. For example, multiple short lengths of hollow fibres may be used, the blind end of each fibre being exposed to the sample whilst the open ends are held by the holder (eg are potted into the plug) and communicate with the filtrate chamber. Conveniently the blind ended fibres diverge away from a central portion of the holder.

In an alternative embodiment using blind ended hollow fibre membranes, short lengths of the fibres are cut and joined together at the apex (thus closing their lumens at that point) into a "teepee"-like shape. The apex is exposed to the sample whilst the opposite ends of the membrane fibres pass through the holder and are exposed on the opposite side thereof.

The filtration means in this embodiment is located within the device by means of the holder which will normally be a plug of cured adhesive. The plug forms a tight fit with the inside surfaces of the conduit lumen. It is essential that the plug or any other holder seals the conduit lumen, as the sample to be filtered could otherwise pass through the gap between the plug and the interior of the conduit. The filter itself is at least partially embedded within the plug.

The plug will normally be formed from adhesive, usually cured adhesive Any material capable of forming a seal with the membrane fibres and the filter chamber may be used.

The adhesive used to form the filter plug of the present invention may be any adhesive material which does not react with the membrane or filter chamber materials in a deleterious manner. Preferably the adhesive material is quick setting, ie cures within minutes, for example under 5 minutes. For certain embodiments adhesive material which cures upon exposure to light is particularly desirable. For example in medical applications it may be preferred to use adhesive which cures upon exposure to blue light, especially UV light.

Suitable adhesive material is commercially available and mention may be made of polymers available from Ablestick Ltd (for example LCM 32, LCM 34 and LCM 35), Bostick Ltd or Dynax Inc (eg 191M) as being suitable UV curing adhesives.

The sensing means can comprise chemical agents such as catalysts, pH indicators, or molecules such as DNA, lectins, antibodies or abzymes (reactive against viral proteins, for example) or enzymes. Alternatively, the sensing means may be electronic, such as a device known as an "electronic nose" which detects the presence and/or concentration of a gas. Optionally, the sensing means can comprise two or more of such devices and/or chemicals/molecules which may act sequentially or together on the same filtered sample.

The sensing means may be localised on a membrane located within the device, usually so that the filtered sample is exposed thereto. In one embodiment a potted membrane (as described above for the filtration means) is provided, the membrane being treated to allow detection of a specific component that may be present in the sample. Suitable examples are given in co-pending PCT Patent Application No PCT/GB95/01834, the disclosures of which are hereby incorporated by reference.

Alternatively, the sensing means may be disposed on or in the filtration means, for example, in the case of a chemical or molecular sensing means, it can be bonded to one side of the filter, such as by covalent or ionic bonding, or by hydrophobic or hydrophilic attraction to the filtration means or can be impregnated therein. It may be desirable for a chemical or molecular sensing means to be attached to the filtration means by covalent bonding, optionally via a spacer molecule, so that the presentation of the sensing means is enhanced, and/or that steric interference is reduced or avoided.

Optionally, the sensing means can be provided in the chamber, and can be presented on the chamber walls, or on beads, rods or the like located within the chamber.

The sensing means can react with a component in the filtered sample so as to effect a colour change in the sensing means or in a substrate optionally present. Thus, the presence/concentration of the component detected can be observed visually or spectrophometrically. In such an embodiment, the device or the chamber may desirably be partially or wholly constructed from transparent or translucent material, such as moulded plastics material.

Preferably, the puncture means comprises a needle, most preferably of very narrow bore.

Embodiments of the device can provide a self contained sampling and assay system, and can function effectively with low volumes of fluid so as to avoid the need to extract large volumes of the fluid.

The fluids to be sampled may flow into the device through surface tension or capillary action without any other force required to draw the body fluids towards the filtration means. However, the device may be used in conjunction with pressure means such as a conventional syringe in order to produce a pressure differential across the filtration means, for example by providing a suction pressure to draw the body fluids through the conduit into the device and/or across the filtration means. Once the fluid has entered the device, the pressurizing means may also be used to induce pressure in the fluid to be filtered thereby speeding up the rate of filtration. The device may also incorporate sealing means to seal the fluid in the device when the fluid is being pressurized, so that more efficient filtration through the membrane is achieved. Advantageously, the sealing means may comprise a cap for the device or a portion of such a cap.

An embodiment of the present invention will now be described by way of example, with reference to the accompanying drawings, in which;

FIG. 7 shows a cross-section an alternative device according to the invention;

FIG. 8 shows a perspective cross-sectional view of the device of FIG. 7; and

FIG. 9 illustrates optional attachments adapted to fit onto the device of FIGS. 7 and 8.

Figure 1:
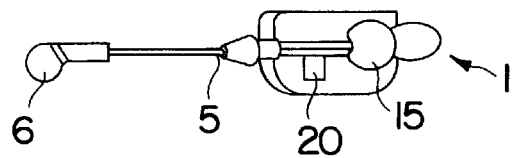
FIG. 1 is a side view of a device according to the invention.
Figure 2:
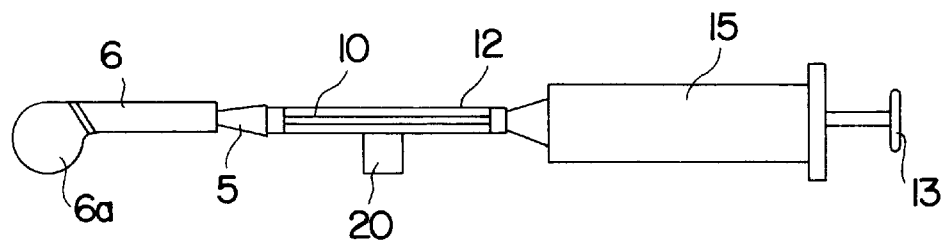
FIG. 2 shows a detailed view of the device shown in FIG. 1.

Referring now to the drawings, a device 1 according to the invention comprises a needle 5 covered by a cap 6. The needle 5 is hollow and its bore communicates with the bore of a hollow membrane fibre 10 enclosed in a housing 12 which provides support to the relatively fragile membrane fibre 10. The hollow membrane fibre 10 is in the form of a hollow tube of exemplary diameter 0.5 mm formed from a membrane filter which can filter out molecules of 1000 Da. One end of the fibre 10 is connected to the needle 5, and the other end of the fibre 10 is connected to a conventional syringe 15.

The housing 12 comprises a hollow tube of clear plastics material of internal diameter 1 mm, and optionally has a generally cuboidal collecting chamber 20 of the same material attached to one side of the housing 12.

The collecting chamber 20 contains glass or plastics beads (not shown) which have sensing means (in this case anti-viral antibodies) attached thereto, optionally by covalent bonding. The choice of sensing means can vary widely according to the component to be detected.

Figure 3:
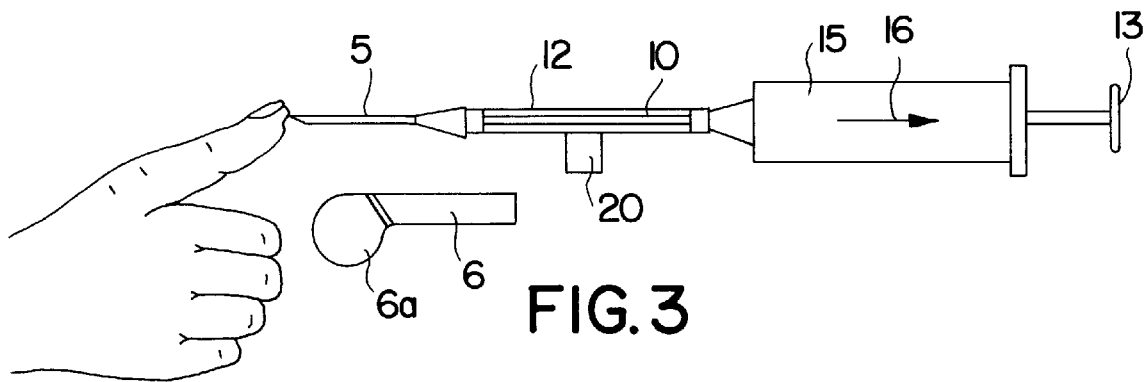
FIG. 3 shows the device in use drawing fluid into the device.
Figure 4:
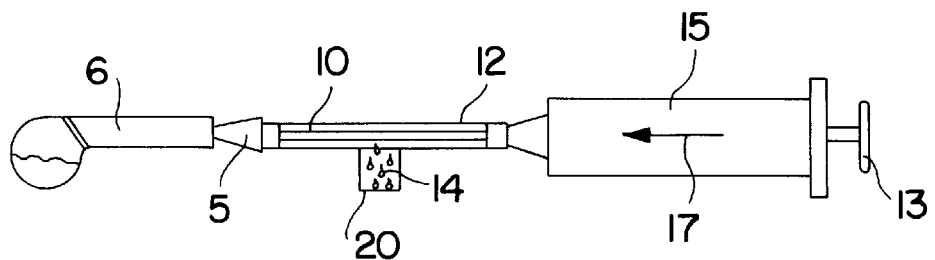
FIG. 4 shows the device in use expelling fluid from the syringe.
Figure 5:
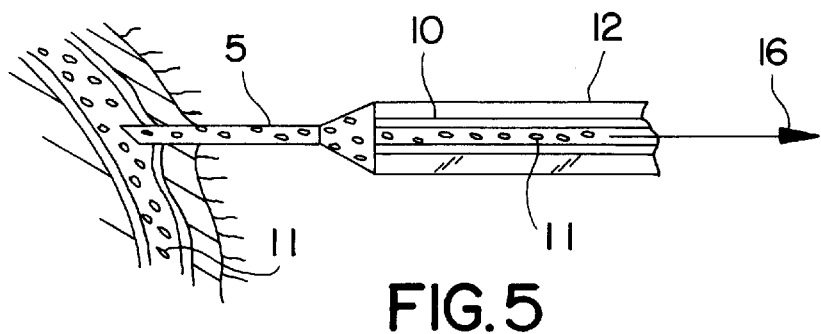
FIG. 5 shows a close up view of the device in use drawing blood from a blood vessel into the device.
Figure 6:
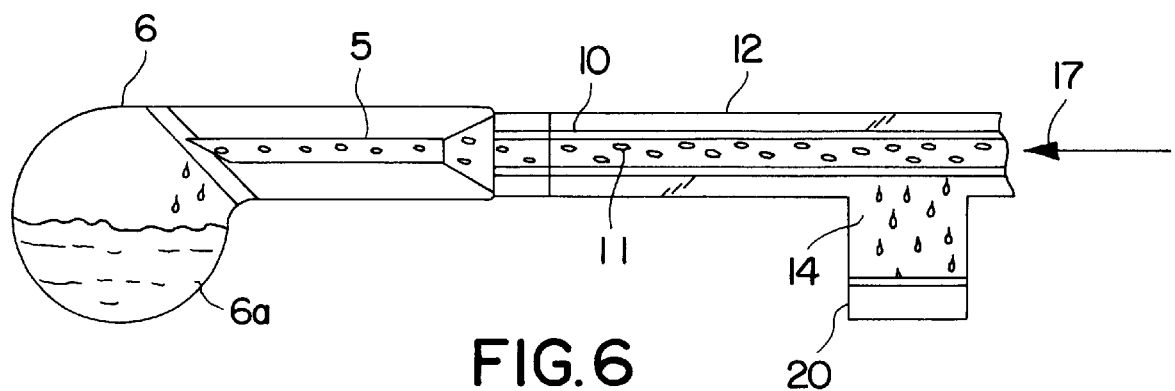
FIG. 6 shows a close up view of the device showing the fluid being forced through the filtration means.

In use, the device 1 is uncapped and the needle 5 is inserted into a patient's thumb (see FIG. 3) or another part of the patient's body, so as to pierce a blood vessel (see FIG. 5). The blood may be allowed to flow through the needle 5 and hollow membrane fibre 10 by capillary action or can be drawn into the device by pulling the plunger 13 of the syringe 15 in the direction of arrow 16 (see FIG. 3), so that blood 11 is collected in the hollow membrane fibre 10. The hollow membrane fibre 10 can have a very narrow bore so that the volume of blood 11 required to fill it can be less than 0.1 $\mu$l.

Once a sufficient quantity of blood 11 is collected in the fibre 10, the plunger 13 of the syringe may be depressed in the direction of arrow 17, pressurizing the blood 11 and forcing it through the membrane of the fibre 10.

The cap 6 can be replaced during this step thereby sealing the bore of the needle 5 at 7 and forcing the blood 11 to pass through the membrane, but replacement of the cap is not necessary. Sufficient pressure can be obtained by depressing the syringe plunger without sealing the bore. Indeed, pressurizing the blood 11 is actually unnecessary since the device can simply be shaken to facilitate filtration.

The blood cells and other blood components too large to pass through the pores of the membrane are retained within the fibre 10 and the serum containing the filtered components 14 is collected in the collecting chamber 20 where it mixes with the glass or plastic beads to which the sensing means are attached. The walls (or a portion thereof) of the chamber 20 can be transparent, and a positive indication of the presence of particular components can be visualised directly by observing eg colour changes in a reagent optionally also present in the chamber. The concentration of the components can be measured by spectrophotometric analysis using conventional methods.

A bulbous head 6a in the cap 6 can be used to contain any fluids passing through the needle bore during the pressurization step.

Modifications and improvements may be incorporated without departing from the scope of the invention. For example, the inner walls of the housing 12 can be inclined from the chamber 20 so that all drops of filtrate coming through the membrane are more efficiently collected in the chamber 20. Alternatively the chamber 20 may be disposed at one end of the device, so that it can be shaken bag hand to encourage movement of drops of filtrate towards the chamber 20.

Referring to FIG. 7, this shows a cross section of an alternative embodiment of a device 1 according to the present invention. Device 1 comprises housing 12 having located therein a filtration means 22 which in this embodiment comprises a hollow fibre membrane shaped into a "U" or hoop the ends of the fibre being embedded within in a solid plug of cured adhesive so that the lumen of the ends are exposed on the opposite side of the plug to the main body of the "U" or hoop. In use the sample enters device 1 via aperture 2, is taken up into housing 12 and exposed to filtration means 22. The fluid sample may be urged across the filtration means 22 by application of pressure, for example by fitting a conventional syringe 15 to device 1 as depicted in FIG. 7 and urging plunger 13 of syringe 15 in the direction of arrow 16. The filtrate cross the hollow fibre membrane, collects in the lumen thereof and passes into collection chamber 20 by running down the lumen to the open ends thereof which are exposed on the opposite side of the plug to the main body of the hoop, facing the collection chamber 20. Collection chamber 20 in this embodiment is that part of housing 12 located above the filtration means 22. The portion of the sample not able to pass through 22 the hollow fibre membrane cannot pass into the collection chamber 20.

The filtrate then comes into contact with sensing means 21. As shown in FIG. 7 sensing means 21 comprises treated hollow fibre membrane 24, the ends of which pass through plugs 25 and 25'. Thus, the filtrate is taken into the internal lumnen of hollow fibre 24, which has been treated with an agent able to detect a component believed to be present within the sample. The presence of that component results in a colour change which is directly visualised through the device, for example exposing the device to UV light.

Optionally the device 1 depicted in FIG. 7 may comprise a puncture means 5 which in the device as illustrated consists of a hypodermic needle having a female luer lock 4 which engages with the male luer lock 4' on the device. Once the sample is taken up into device 1, puncturing means 5 may be removed and disposed of for safety, to avoid the accidental puncturing of the operator etc.

FIG. 8 shows in more detail a perspective cross sectional view of the device of FIG. 7 and includes a non-return valve 23 located within housing 12 to prevent the inadvertent expulsion of the sample, for example by depressing syringe plunger 13. In the embodiment illustrated the syringe 15 is removable so that device 1 can be analysed without the continued presence of the syringe. Optionally a non-return valve may be located at both ends of the device to prevent leakage of the fluid sample.

FIG. 9 illustrates alternative optional attachments to device 1. FIG. 9a is a biopsy needle and FIG. 9b is a small bore needle. Both puncture means illustrated in FIGS. 9a and 9b are provided with a female luer lock 4 adapted to engage with the male luer lock 4' present on device 1. As an alternative to the puncture means 5, it is possible to provide a soft tip fluid collection tube as illustrated in FIG. 9c. Again, the female luer lock 4 is adapted to engage with the male luer lock 4' of device 1 in FIG. 8. The soft tip fluid collection tube of FIG. 9c may be used to facilitate collection of fluids in locations where the close proximity of device 1 may be difficult, for example to collect tear fluid from the eye etc.

In both FIGS. 7 and 8 the filtration means and sensing means rely upon adhesive plugs to maintain their positions within housing 12. The adhesive plugs, for example formed from LCM 34 of Ablestick Ltd, form a close fit with the internal surface of the lumen of housing 12. Desirably housing 12 is of transparent material.

I claim:

1. A portable device for sampling fluid comprising:

a syringe;

a housing having an interior and exterior wall and a first and second end, said first end attached to said syringe;

a collection chamber contained in said housing;

filtration means comprised of at least one U-shaped hollow fiber membrane contained in said housing between said collection chamber and said second end;

puncture means attached to said second end of said housing, said housing in fluid communication with said syringe and said puncture means;

sensing means contained in said housing between said collection chamber and said first end of said housing, said sensing means comprised of a further hollow fiber membrane with first and second ends each connected to a first and second plug, respectively, said first and second plugs contacting said interior wall of said housing, said further hollow fiber membrane containing a sensing agent;

wherein said device is arranged so that a sample is collected through said puncture means, communicated to said filtration means and passed through said at least one U-shaped hollow fiber membrane to said collection chamber, then passed through said further hollow fiber membrane and said sensing means before being passed to said syringe.

2. A device as claimed in claim 1 wherein said puncture means is a hypodermic, biopsy or small bore needle.

3. A device as claimed in claim 1 having a non-return valve.

* * * * *

UNITED STATES PATENT AND TRADE MARK OFFICE
CERTIFICATE OF CORRECTION

PATENT NO. : 5,919,356
DATED : July 6, 1999
INVENTOR(S) : Hood

It is certified that error appears in the above-identified patent and that said Letters Patent is hereby corrected as shown below:

Title Page: Item [56], under FOREIGN PATENT DOCUMENTS, the fourth reference listed should read -- 41 32 480 A1    4/1993    Germany --

Signed and Sealed this

First Day of February, 2000

Attest:

Q. TODD DICKINSON

*Attesting Officer*        *Acting Commissioner of Patents and Trademarks*

UNITED STATES PATENT AND TRADEMARK OFFICE
CERTIFICATE OF CORRECTION

PATENT NO. : 5,919,356
DATED : July 6, 1999
INVENTOR(S) : Robert Gordon Hood

It is certified that error appears in the above-identified patent and that said Letters Patent is hereby corrected as shown below:

Column 5, line 5, delete "FIG. 9 illustrates" and insert --FIGS. 9A-C illustrate--.

Column 6, line 54, delete "FIG. 9 illustrates" and insert --FIGS. 9A-C illustrate--.

Column 6, line 55, change "9a" to --9A--.

Column 6, line 55, change "9b" to –9B--.

Column 6, lines 56 and 57, change "9a and 9b" to --9A and 9B--.

Column 6, line 60, change "9c" to --9C--.

Column 6, line 63, change "9c" to --9C--.

Signed and Sealed this

Seventh Day of November, 2000

Attest:

Q. TODD DICKINSON

*Attesting Officer*          *Director of Patents and Trademarks*